US007754677B2

(12) United States Patent
Khoo et al.

(10) Patent No.: US 7,754,677 B2
(45) Date of Patent: Jul. 13, 2010

(54) COMPOSITION AND METHOD FOR REDUCING DIARRHEA IN A MAMMAL

(75) Inventors: Christina Khoo, Lawrence, KS (US);
Kathy Lynn Gross, Topeka, KS (US);
Dennis Jewell, Lawrence, KS (US);
Karen Wedekind, Meriden, KS (US);
Steven Zicker, Lawrence, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 0 days.

(21) Appl. No.: 10/729,450

(22) Filed: Dec. 5, 2003

(65) Prior Publication Data
US 2005/0124576 A1    Jun. 9, 2005

(51) Int. Cl.
*A01N 37/18*    (2006.01)

(52) U.S. Cl. .............................. 514/2; 514/23; 514/54; 424/442

(58) Field of Classification Search ............... 424/78.01, 424/442, 867
See application file for complete search history.

(56) References Cited

U.S. PATENT DOCUMENTS

| | | | |
|---|---|---|---|
| 5,294,458 A | 3/1994 | Fujimori | |
| 5,444,054 A | 8/1995 | Garleb et al. | |
| 5,744,134 A | 4/1998 | Paul | |
| 5,939,309 A | 8/1999 | Suwa et al. | |
| 5,952,033 A | 9/1999 | Anatharaman et al. | |
| 5,968,569 A | 10/1999 | Cavadini et al. | |
| 6,051,260 A | 4/2000 | Liska et al. | |
| 6,156,355 A * | 12/2000 | Shields et al. ................. | 426/74 |
| 6,180,099 B1 | 1/2001 | Paul | |
| 6,197,361 B1 | 3/2001 | Anantharaman et al. | |
| 6,203,797 B1 | 3/2001 | Perry | |
| 6,241,983 B1 | 6/2001 | Paul et al. | |
| 6,270,811 B1 | 8/2001 | Fregonese | |
| 6,468,525 B1 | 10/2002 | Watson et al. | |
| 6,488,970 B1 | 12/2002 | Hora | |
| 6,544,568 B2 | 4/2003 | De Simone et al. | |
| 6,592,863 B2 | 7/2003 | Fuchs et al. | |
| 6,689,812 B2 | 2/2004 | Peet et al. | |
| 6,706,287 B2 | 3/2004 | Ranganathan et al. | |
| 6,737,089 B2 * | 5/2004 | Wadsworth et al. ......... | 424/777 |
| 2002/0044988 A1 | 4/2002 | Fuchs et al. | |
| 2002/0127211 A1 | 9/2002 | Brassart et al. | |
| 2002/0182276 A1* | 12/2002 | Wadsworth et al. ......... | 424/765 |
| 2002/0183389 A1 | 12/2002 | Peet et al. | |

FOREIGN PATENT DOCUMENTS

EP    0 674 842 A1    10/1995

EP    0674842    10/1995

OTHER PUBLICATIONS

Chandler, M, In Practice, Oct. 2002, vol. 24, No. 9, pp. 538-531 & 533.*
Klimberg et al, Arch Surg, 1990, vol. 125, pp. 1040-1045.*
Taber's Cyclopedic Medical Dictionary, 1997, F.A. Davis Company, 18th Edition, pp. 535-536.*
"Glutamine" The World's Healthiest Foods. The George Mateljan Foundation. Retrieved: Aug. 14, 2008 <http://www.whfoods.com/genpage.php?tname=nutrient&dbid=122>.*
Hamada et al, Journal of Chromatography A, (1998) vol. 827, pp. 319-327.*
Hickman, MA, Clinical Techniques in Small Animal Practice. (1998), vol. 13, No. 4, pp. 211-216.*
Guilford, WG. Journal of Small Animal Practice (1994), vol. 35, pp. 620-624.*
Nappert, "Intestinal metabolism of glutamine and potential use of glutamine as a therapeutic agent in diarrheic calves", Journal of the American Veterinary Medical Associate, 1997, pp. 547-551, vol. 211, No. 5.
Kanauchi, "Effects of germinated barley foodstuff in preventing diarrhea and forming normal feces in ceco-colectomized rats", Bioscience Biotechnology and Biochemistry, vol. 62, No. 2, Feb. 1998, pp. 366-368.
Correa-Matos, "Fermentable substrate reduces recovery time and improves intestinal function in piglets following *Salmonella* infection", FASEB Journal, vol. 15, No. 4, Mar. 7, 2001, p. A642, XP009045249, and Annual Meeting of the Federation of American Societies for Experimental Biology on Experimental Biol, Mar. 31-Apr. 4, 2001, Orlando, FL.
Shoda, "Therapeutic efficacy of glutamine and N-3 poly-unsaturated fatty acid supplementation in profound hypoglycemia in rat model of lectininduced diarrhea", Gastroenterology, vol. 114, No. 4 Part 2, Apr. 15, 1998, pp. A908-A909, and Digestive Diseases Week and the 99$^{TH}$ Annual Meeting of the American Gastroenterological Association, May 12-22, 1998, New Orleans, LA.
Correa-Matos, "Fermentable fiber reduces recovery time and improves intestinal function in piglets following *Salmonella typhimurium* infection."
Simpson, "Diet and large intestinal disease in dogs and cats.", The Journal of Nutrition, Dec. 1998, pp. 2717S-2722S, vol. 62, No. 12.
Hara, "Antibacterial Actions of Tea Polyphenols and Their Practical Applications in Humans", *Phytochemicals and Phytophermaceuticals* (Shahidi and Ho, eds), Ch. 19, 214-21 (200).
Loubinoux, et al, "Sulfate-reducing bacteria in human feces and their association with Inflammatory bowel diseases", *FEMS Microbiology Ecology* 40 :197-112 (2002).

(Continued)

*Primary Examiner*—Allison M Ford
(74) *Attorney, Agent, or Firm*—Shannon McGarrah

(57) ABSTRACT

A composition suitable for mammalian oral ingestion in a mammal having GI tract inflammation comprising an anti-diarrhea effective amount of glutamine, fermentable fiber(s), antioxidant(s), and omega-3 fatty acid(s).

4 Claims, No Drawings

OTHER PUBLICATIONS

Gibson, et al, "Growth and activities of sulphate-reducing bacteria in gut contents of healthy subjects and patients with ulcerative colitis", *FEMS Microbiology Ecology* 86:103-112 (1991).

Hirayama, "Novel physiological functions of oligosaccharides", *Pure Appl. Chem.*, 74(7):1271-1279 (2002).

Nappert, et al., "Intestinal metabolism of glutamine and potential use of glutamine as a therapeutic agent in diarrheic calves", *JAVMA* 211(5):547-553 (1997).

Kanauchi, et al., "Effects of Germinated Barley Foodstuff in Preventing Diarrhea and Forming Normal Feces in Ceco-colectmoized Rats", *Biosci. Biotechnol. Biochem.*, 62(2):366-368 (1998).

Correa-Matos, et al., "Fermentable Fiber Reduces Recovery Time and Improves Intestinal Function in Piglets Following *Salmonella typhimurium* Infection", *FASEB Journal* 15(4): 1845-1852 (2001).

Simpson, J.W., "Diet and Large Intestinal Disease in Dogs and Cats", *J. Of Nutr.* 128(12):2717S-2722S (1998).

Correa-Matos, et al., "Fermentable substrate reduces recovery time and improves intestinal function in piglets following *Salmonella* infection", *FASEB Journal* 15(4):A642 (2001).

Shoda, et al., "Therapeutic efficacy of glutamine and N-3 polyunsaturated fatty acid supplementation in profound hypoglycemia in rat model of lectin-induced diarrhea", *Gastroenterology* 114(4):A908-A909 (1998).

* cited by examiner

COMPOSITION AND METHOD FOR REDUCING DIARRHEA IN A MAMMAL

BACKGROUND OF THE INVENTION

Maintaining the well being of the GI tract of a mammal is a very desirable goal. Particularly annoying are inflammatory conditions of the GI tract. Some of the signs of inflammation of the GI tract include acute or chronic diarrhea, soft stools, blood in stool, vomiting, poor nutrient digestion and absorption, weight loss and poor appetite. Diseases such as gastritis, enteritis, colitis, inflammatory bowel disease, ulcers, certain types of cancer and other conditions are known to have GI inflammation as a main component.

We have found that a mixture of certain materials can bring about the amelioration of the principle signs of GI inflammation such as diarrhea. The frequency of eliminations as well as the quality of the elimination can be substantially improved when GI tract inflammation is improved, particularly in a companion pet such as a cat, when appropriate levels of glutamine, fermentable fiber(s), antioxidant(s) and omega (n)-3 fatty acids are orally administered to the mammal.

SUMMARY OF THE INVENTION

In accordance with the invention, there is a composition suitable for mammalian oral ingestion in a mammal having GI tract inflammation comprising an anti-diarrhea effective amount of a combination of glutamine, fermentable fiber(s), antioxidant(s) and omega-3 fatty acid(s).

A further aspect of the invention is a method for managing diarrhea in a mammal having GI tract inflammation comprising orally administering to the mammal a composition described above.

DETAILED DESCRIPTION OF THE INVENTION

Glutamine is a well known as a material which is important for lymphocytes to proliferate and important as a nutrient for intestinal cells. Glutamine is also a precursor for glutathione, a natural antioxidant in the body. All wt % disclosed here for any constituent are on the basis of a daily diet for the mammal. All numbers are calculated on a dry matter basis.

The quantity of glutamine is a minimum of about 0.1, 0.15 or 0.2 wt %. The maximum generally does not exceed about 5, 4 or 3 wt %.

Fibers which can be employed are those which are moderately fermentable, highly fermentable or blends of the two. Low or non-fermentable fibers can also be added at low levels without impacting the formulation.

We have shown that certain prebiotic fiber ingredients when fermented by existing bacteria from the GI tract of dogs and cats produce high levels of butyrate and other short chain fatty acids which would acidify the GI tract and reduce the growth of pathogens. Prebiotic fibers that produce high levels of butyrate include but are not limited to mannan-oligosaccharide, pectin, xylooligosaccharide, burdock, beet pulp, inulin, galactose, other xylans, fructans, dextrans, beta glucan, resistant starches, polysaccharide from gums, etc., should be present at levels between about 0.5-20 wt % of diet with the preferred levels between about 1-5 wt %. Gums may include gums produced by microorganisms such as gellan gum, xanthan or gums produced by plants such as acacia. The blend is preferably formulated based on high butyrate production and moderate fermentability based on volatile fatty acids (VFA) production and organic matter disappearance to help maintain optimal GI health. The composition can include at least about 10-60% of a moderately fermentable fiber and about 20-40% of a highly fermentable fiber. These fibers should be chosen such that the butyrate production of these fibers is high, between about 5-40% of total VFA. Moderately fermentable fibers are defined as having an organic matter disappearance of from about 15 to 60 percent when fermented by fecal bacteria in vitro for a 24 hour period. That is, from about 15 to 60 percent of the total organic matter originally present is fermented and converted by the fecal bacteria. Highly fermentable fibers have greater than a 60% disappearance rate.

Antioxidants can also be employed in the compositions and methods. Vitamin E, C and blends thereof can be employed. Any precursors of these vitamins can be employed, such as tocopheryl acetate and sodium ascorbate. Vitamin E is a minimum of about 0.1, 0.2 or 0.4 wt % and generally does not exceed a maximum of about 3, 2 or 1 wt % of the diet. Vitamin C is a minimum of about 0.1, 0.2 or 0.4 wt % and generally does not exceed a maximum of about 3, 2, or 1% of the diet.

Omega-3 fatty acids are well known dietary constituents and are primarily found in fats and oils, particularly fish oils such as menhaden, salmon and the like. Principle constituents of the omega-3 fatty acid are ecosapentaenoic acid (EPA), docosahexanoic acid (DHA) and alpha-linolenic acid (ALA). The quantities of omega-3 fatty acids are generally a minimum of about 0.1, 0.2 or 0.5 wt % and generally do not exceed a maximum of about 3, 2 or 1 wt %. Also generally present in the fats and oils are omega-6 fatty acids. The proportion of omega-6 fatty acid when present to omega-3 fatty acid on a weight basis is from about 0.5:1 to 6:1, preferably about 2:1 to 4:1.

The following examples illustrate the benefits to be achieved using the composition of the invention in managing diarrhea in a mammal. The mammal has or can have GI tract inflammation, preferably inflammatory bowel disease.

EXAMPLE 1

In the following study, 12 cats with inflammatory bowel disease (IBD) were fed 2 varieties of food for a period of 2 weeks each. Six cats were fed Food A and 6 cats fed Food B for 2 weeks, followed by a crossover. Stool quality was monitored daily and the score based on a 1-5 scale, with 1 being runny and watery and 5 being hard and formed, see scores below. Stools from cats with IBD typically are 1 or 2.

Stool Monitoring Scoring

1: watery

2: soft, unformed

3: soft, formed, moist

4: hard, formed, dry

5: hard, dry pellets

Table 1 shows the effect of diets on the stool quality of cats with chronic diarrhea. The table show the percent of stools with scores of 1-5. The first canned Food A contained 3% of a fiber with low fermentability, less than 15%, and the canned Food B contained 1.5% of a fiber with high fermentability, above about 60% fermentability. The nutrient content of the foods are listed below.

|  | Food A<br>Low<br>fermentable<br>fiber food | Food B<br>High<br>fermentable<br>fiber food |
| --- | --- | --- |
| Moisture | 72.69 | 72.58 |
| Protein-Kjeldahl | 8.24 | 7.94 |
| Fiber, Crude | 0.3 | 0.2 |
| Crude fat by acid hydrolysis | 9.58 | 9.85 |

Results

The results show that feeding Food B containing a highly fermentable fiber source improved the stool quality of the cats from having 42% stools scoring 1's and 2's to only 15% scoring 1's and 2's.

TABLE 1

| Stool quality<br>Score | % of Stools | |
| --- | --- | --- |
|  | Food A<br>Low fermentable<br>fiber food | Food B*<br>High fermentable<br>fiber food |
| 1 | 11 | 2 |
| 2 | 31 | 13 |
| 3 | 41 | 45 |
| 4 | 10 | 22 |
| 5 | 7 | 14 |

*4% of stools were not available for grading

EXAMPLE 2

Table 2 shows the data from a study where the same cats as in example 1 were fed 2 different foods. Both foods contained similar levels of prebiotic fibers and Omega-3 fatty acids. Food C contained added glutamine and antioxidants whereas Food D did not contain added glutamine or antioxidants. Half the cats were fed Food C for 2 weeks and the other half were fed Food D. This was followed by a washout of one week for all the cats. They were then crossed over to the other food for an additional 2 weeks. The results in Table 2 show that when the cats were fed Food C that included glutamine and high antioxidants, the stool quality was significantly improved (0% stool score of 1 and 2) compared to the stool quality when the cats were fed Food D, the diet without added glutamine and antioxidants (7% stool with score of 1 and 2). Food C has significantly better results in stool quality, 0% stool scores of 1 and 2, compared to Food A having 42% of its stool score 1 and 2. Food C is also significantly better than Food B having 15% of stool scores of 1 and 2. Food C is also significantly better than Food D which has 7% of stool scores 1 and 2. Food C has all the significant components of this invention: glutamine, antioxidant, fermentable fiber and n-3 fatty acids. Foods A, B and D were all missing at least one of these components.

The nutrient content of the food is listed below.

| Formula | All options<br>(Food C) | All options except<br>glutamine and<br>antioxidant<br>(Food D) |
| --- | --- | --- |
| Moisture % | 75–76 | 75–76 |
| Protein-Kjeldahl % | 10 | 10.1 |

-continued

| Formula | All options<br>(Food C) | All options except<br>glutamine and<br>antioxidant<br>(Food D) |
| --- | --- | --- |
| Crude Fiber % | 0.2 | 0.4 |
| Ash % | 1.49 | 1.69 |
| Crude Fat % | 4–6 | 4–6 |
| Insoluble fiber % | 1–1.5 | 1–1.5 |
| Soluble fiber % | 0.1–0.3 | 0.1–0.3 |
| Omega 3 (calc) | 0.13 | 0.06 |
| Omega 6 (calc) | 1.51 | 0.46 |
| ascorbic acid µg/g | 30–50 | 4–10 |
| total tocopherols µg/ml | 300–400 | 30–50 |

TABLE 2

| Stool quality<br>score | Percentage of Stools | |
| --- | --- | --- |
|  | Food C<br>[all options] | Food D [all options except<br>glutamine & antioxidants] |
| 1 | 0 | 0 |
| 2 | 0 | 7 |
| 3 | 29 | 67 |
| 4 | 58 | 27 |
| 5 | 13 | 1 |

The data shows that the diet with added glutamine and antioxidants continues to sustain the improvement in stool quality in these cats.

EXAMPLE 3

The next experiments show that the glutamine source that was used in the previous example is bioavailable and is able to stimulate the immune function. Glutamine is an important nutrient to the intestinal tract as it is the major fuel source for enterocytes and lymphocytes. A majority of the glutamine in the diet is absorbed by cells of the intestine as well as immune cells in the intestine.

In one experiment, a source of glutamine was tested to see if it was bioavailable and able to deliver adequate glutamine to the intestinal cells. The source of glutamine was a wheat hydrolysate with an enrichment of 30% glutamine. A dose response study was carried out in 6 dogs to see if increasing levels of the glutamine source (0, 0.5, 1.0, 2% glutamine content) was detected in the plasma after feeding the diet.

TABLE 3

Change in postprandial plasma glutamine in animals fed foods supplemented with different levels of glutamine.

| % supplemented<br>glutamine | % Change in plasma<br>glutamine from control |
| --- | --- |
| 0.5% | 3 |
| 1.0% | 10 |
| 2.0% | 15 |

The data shows that there was an increasing response to the increased levels of glutamine in the diet, particularly 30 min after the meal. This shows that the glutamine is available to the blood stream after extraction by the intestinal cells.

In a further experiment, the efficacy of glutamine as a immune-modulator was examined. 20 Beagle dogs were randomly allocated into 4 groups receiving either basic diet or basic diet supplemented with 1%, 2%, or 4% glutamine. Blood samples were drawn in heparinized tubes from animals 2 hrs after their last feeding on day 1 and 16. Samples were prepared for immune measurement. (T cell proliferation assay).

T-cell proliferation assay. Peripheral blood leukocytes (PBL) in each blood sample were counted using Nova Celltrak II (Beckman Coulter Corp., Fla.). Blood was diluted (1:20) with supplemented media. Diluted blood was plated, in triplicate, in 96 well cell culture plates with the following mitogens diluted in supplemented media: Concanavalin A (0.5 μg/ml, 2.5 μg/ml. Plates were incubated in a humidified incubator containing 7% $CO_2$ at 37° C. for 72 hrs. Cellular DNA was Ci/well [pulse labeled 18 hrs before harvesting with 1 $^3$H] thymidine. Cellular DNA was harvested on glass fiber paper using a cell harvester (Skatron Instruments Inc., Va.) and suspended with 1.5 ml scintillation cocktail. [$^3$H] thymidine uptake was quantified as counts per minutes (CPM) using TriCarb 2100TR Liquid Scintillation Analyzer (Packard BioScience Company, Ill.). Counts were normalized to CPM/10,000 cells to account for variation in PBL concentrations.

Effect of Glutamine on Lymphocyte Proliferation

Concanvalin A (Con A) is a polyclonal T-cell mitogen. In the presence of Con A mitogen, overall analysis showed a significant effect of diet, but no effect of Con A dose, or dietary treatment by Con A dose interaction. Thus, the data were collapsed across the different doses of Con A to show the proliferative response of lymphocytes dependent on percentage of glutamine supplemented in the diet.

TABLE 4

Proliferation of T cell lymphocyte in response to ConA mitogen

| Food | T cell proliferation ($\log_{10}$ cpm) |
|---|---|
| No supplemented glutamine | 4.7 |
| 1% supplemental glutamine | 5 |
| 2% supplemental glutamine | 4.8 |
| 4% supplemental glutamine | 4.5 |

There was a significant main effect of dietary treatment (P<0.01). Dietary supplementation of 1% glutamine showed maximum lymphocyte proliferation which was significantly different from the control group (P<0.05). Dogs supplied with 1% and 2% glutamine showed similar increases in lymphocyte proliferation. There was a significant difference between these groups and the proliferative response of lymphocytes from animals supplemented with 4% glutamine in their diet (P<0.01). This indicates that supplementation with 1-2% glutamine enhances overall T-lymphocytes proliferation. However, 4% glutamine is not additionally beneficial in this respect.

The invention claimed is:

1. A method for treating diarrhea in a cat suffering from inflammatory bowel disease comprising feeding said cat a diet comprising on a dry weight basis:
   from about 30 to about 50 μg ascorbic acid per gram of pet food composition;
   1.5% by weight omega-6 fatty acid(s);
   from 4% to 6% by weight crude fat;
   from 0.1% to 5% by weight glutamine;
   from 0.5% to 20% by weight fermentable fiber(s);
   from 0.1% to 3% by weight antioxidant(s) in addition to the about 30 to about 50 μg ascorbic acid per gram of pet food composition; and
   from 01% to 3% by weight omega-3 fatty acid(s).

2. A method according to claim 1, wherein said diet comprises:
   0.2% to 3% by weight glutamine;
   1% to 5% by weight fermentable fiber;
   0.2% to 2% by weight antioxidants;
   0.2% to 2% by weight omega-3 fatty acids.

3. A method according to claim 1, wherein the antioxidants comprise vitamin C, vitamin E, or combinations thereof.

4. A method according to claim 1, wherein the diet is effective when fed to said cat to treat watery runny stool and soft unformed stool.

* * * * *